US00PP08805P

United States Patent [19]

VandenBerg

[11] Patent Number: Plant 8,805

[45] Date of Patent: Jun. 28, 1994

[54] CHRYSANTHEMUM PLANT NAMED WHITE CORRIDA

[75] Inventor: Cornelis P. VandenBerg, Salinas, Calif.

[73] Assignee: Yoder Brothers, Inc., Barberton, Ohio

[21] Appl. No.: 35,590

[22] Filed: Mar. 23, 1993

[51] Int. Cl.[5] ..... A01H 5/00

[52] U.S. Cl. ..... Plt./82.1

[58] Field of Search ..... Plt. 76, 82.4, 82.1

[56] References Cited

U.S. PATENT DOCUMENTS 4,616,099 10/1986 Sparkes ..... 47/58 X

OTHER PUBLICATIONS

Sigurbjornsson, B., "Chapter 8, Induced Mutations", *Crop Breeding,* 1983, ASA, CSSA, pp. 153–176.

Broertijes, C., et al., (1978) "Chrysanthemum" *Mutation Breeding Methods in the Improvement of Vegetatively Propagated Crops* Elsevier Science Publishing Company, New York pp. 162–175.

Dovrick, G. J., et al (1966) "The Induction of Mutations in Chrysanthemums Using X and Gamma Radiations" *Euphytica* 15, pp. 204–210.

Gosling, S. G., (ed.) "Sporting and Radiation" *The Chrysanthemum Manual,* 1979 Nat. Chrysanth. Soc., Whetstone, London, pp. 329–336.

Searle, S. A., et al., (1968) "Use of Gamma and X Rays" *Chrysanthemums the Year Round* Blandford Press, Ltd., London, pp. 27–29.

Broertjes, C., (1966) "Mutation Breeding of Chrysanthemums" *Euphytica* 15, pp. 156–162.

Broertjes, C., et al., (1980) "A Mutant of a Mutant of a Mutant of a . . . Irradiation of Progressive Radiation Induced Mutants in a Mutation Breeding Programmeurth *Chrysanthemum morifolium*" Euphytica 29, pp. 525–530.

Chan, A. R., (1966) "Chrysanthemum and Rose Mutations Induced by X Rays" J. Am. Soc. Hort. Sci. 88, pp. 613–620.

*Primary Examiner*—James R. Feyrer

*Attorney, Agent, or Firm*—Foley & Lardner

[57] ABSTRACT

A Chrysanthemum plant named White Corrida particularly characterized by its flat capitulum form; spooned anemone capitulum type; white ray floret color; diameter across face of capitulum of 76 to 83 mm when fully opened, when grown as a single stem cut mum; photoperiodic flowering response to short days when grown in Salinas, Calif., is 48 to 51 days after start of short days. Flowering response in Bogota, Colombia is 67 to 68 days; plant height is 69 to 94 cm when grown in Salinas with 17 to 18 long days prior to start of short days; height is 104 cm when grown in Bogota with 21 long days prior to start of short days; peduncle length of the first lateral at flowering after removing the apical bud without growth regulator applications is 5 to 8 cm when grown in Salinas, and 8 cm when grown in Bogota. Peduncle length of the fourth lateral at flowering is 8 to 10 cm when grown in Salinas, and 10 to 13 cm when grown in Bogota; and excellent tolerance to low night temperatures for bud initiation and flower development.

1 Drawing Sheet

The present invention comprises a new and distinct cultivar of Chrysanthemum, botanically known as *Dendranthema grandiflora,* and referred to by the cultivar name White Corrida.

White Corrida, identified as 3555 (86-910C01), is a product of a mutation induction program. The new cultivar was discovered and selected by Cornelis P. VandenBerg on Nov. 28, 1990, in a controlled environment in Salinas, Calif., as one flowering plant within a flowering block established as rooted cuttings from stock plants which had been exposed as unrooted cuttings to an X-ray source of 1500 rads in Fort Myers, Fla., on Jun. 28, 1990.

The irradiated parent cultivar was the cultivar identified as Corrida, disclosed in my Plant Patent application Ser. No. 07/745,700, now U.S. Plant Pat. No. 8,180. Corrida can be described as a spray cut mum with a flat capitulum form; spooned anemone capitulum type; light purple ray floret color; diameter across face of capitulum of 76 to 83 mm when fully opened; flowering response period of 48 to 55 days after start of short days in Salinas, Calif., and of 64 to 70 days in Bogota, Colombia; plant height of 69 to 91 cm when grown in Salinas with 14 to 18 long days prior to start of short days, and 102 to 117 cm when grown in Bogota with 21 long days prior to start of short days; and excellent tolerance to low night temperatures for bud initiation and flower development. The foregoing description of Corrida has a somewhat wider range of measurements than the description of Corrida in the pending application noted. This is based on the continued flowering trials of Corrida after preparing and filing the application for Corrida.

The irradiation program resulting in White Corrida had as its primary objective the expansion of color ranges of the parent cultivar Corrida. The irradiation program comprised irradiating cuttings of the parent cultivar at irradiation levels of 1500, 1750 and 2000 rads. A total of 706 cuttings harvested from a total of 225 irradiated plants were planted on Sep. 24, 1990, Sep. 17, 1990 and Sep. 17, 1990, respectively. Of these, 6 initial selections were made, which selections were then revegetated and reflowered. Three consecutive flowerings resulted in discarding 2 of the original 6 selections on Aug. 9, 1991, while 3 codes were retained as PI (Possible Introduction) status. One code was reselected under code number 1090 on Jul. 16, 1991 and also given PI status. The original selection which was reselected (code 3556) was discarded from the program on Aug. 9, 1991. The three retained codes and the reselected code were further tested in Salinas, Calif., and in Bogota, Colombia, ultimately resulting in discarding two of these codes, and the decision to introduce the reselected code 1090 as Coral Corrida and code 3555 as White Corrida. Coral Corrida is disclosed in a pending application.

The first act of asexual reproduction of White Corrida was accomplished when vegetative cuttings were taken from the original selection in January 1990 in a controlled environment in Salinas, Calif., by technicians working under supervision of Cornelis P. VandenBerg.

Horticultural examination of controlled flowerings of successive plantings has shown that the unique combination of characteristics as herein disclosed for White Corrida are firmly fixed and are retained through successive generations of asexual reproduction.

White Corrida has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Columbia, under greenhouse conditions which approximate those generally used in commercial greenhouse practice. The low night temperature tolerance was determined in repeated flowerings in Bogota, Colombia at temperatures as low as 5–10 degrees Celsius.

The following traits have been repeatedly observed and are determined to be basic characteristics of White Corrida, which, in combination, distinguish this Chrysanthemum as a new and distinct cultivar:

1. Flat capitulum form.
2. Spooned anemone capitulum type.
3. White ray floret color.
4. Diameter across face of capitulum of 76 to 83 mm when fully opened, when grown as a single stem spray cut mum.
5. Photoperiodic flowering response to short days when grown in Salinas, Calif., is 48 to 51 days after start of short days. Flowering response in Bogota, Colombia is 67 to 68 days.
6. Plant height is 69 to 94 cm when grown in Salinas with 17 to 18 long days prior to start of short days; height is 104 cm when grown in Bogota with 21 long days prior to start of short days.
7. Peduncle length of the first lateral at flowering after removing the apical bud without growth regulator applications is 5 to 8 cm when grown in Salinas, and 8 cm when grown in Bogota. Peduncle length of the fourth lateral at flowering is 8 to 10 cm when grown in Salinas, and 10 to 13 cm when grown in Bogota.
8. Excellent tolerance to low night temperatures for bud initiation and flower development.

The accompanying photographic drawing is a side view of a single stem cut spray mum of White Corrida, with the colors being as nearly true as possible with illustrations of this type.

Of the commercial cultivars known to the inventor, the most similar in comparison to White Corrida is the parent cultivar Corrida. All traits of White Corrida are similar to those of Corrida, except for the ray floret color and the plant height. White Corrida has a white ray floret color, while Corrida has a light purple ray floret color. In several of our flowering trials, White Corrida had a taller plant height of 3 to 5 cm when compared with Corrida.

In the following description color references are made to The Royal Horticultural Society Colour Chart. The color values were determined on plant material grown as a single stem spray cut mum in Salinas, Calif. on Dec. 15, 1992.

Classification:

*Botanical.*—*Dendranthema grandiflora* cv White Corrida.

*Commercial.*—Flat spooned anemone cut spray mum.

Inflorescence

A. Capitulum:

*Form.*—Flat.

*Type.*—Spooned anemone.

*Diameter across face.*—76 to 83 mm when fully opened.

B. Corolla of ray florets:

*Color (general tonality from a distance of three meters).*—White.

*Color (upper surface).*—155D to clear white.

*Color (under surface).*—155D to clear white.

*Shape.*—Base tubular, apex flattened and spoon-like, with varying spoon length.

C. Corolla of disc florets (anemone cushion):

*Color (mature).*—12B.

*Color (immature).*—150A to 150B.

D. Reproductive organs:

*Androecium.*—Present on disc florets only; scant pollen.

*Gynoecium.*—Present on both ray and disc florets.

PLANT

A. General appearance:

*Height.*—69 to 94 cm when grown in Salinas with 17 to 18 long days prior to start of short days; height is 104 cm when grown in Bogota with 21 long days prior to start of short days.

B. Foliage:

*Color (upper surface).*—147A.

*Color (under surface).*—147B.

I claim:

1. A new and distinct Chrysanthemum plant named White Corrida, as described and illustrated.

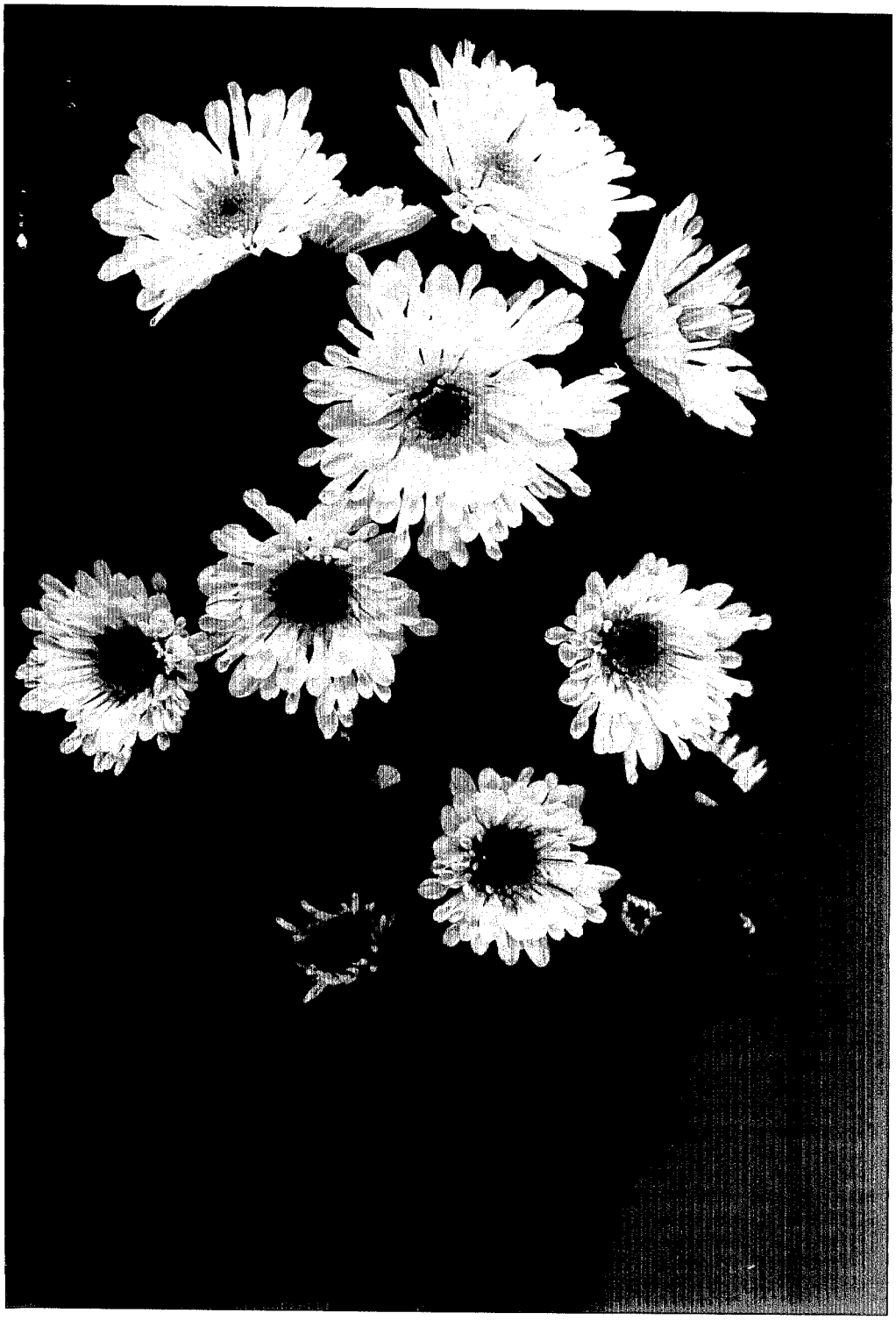

* * * * *